US011419790B2

(12) United States Patent
Yodfat et al.

(10) Patent No.: US 11,419,790 B2
(45) Date of Patent: Aug. 23, 2022

(54) AUTOMATIC DEVICE FOR TRANSFERRING FLUID

(71) Applicant: Roche Diagnostics Operations, Inc., Indianapolis, IN (US)

(72) Inventors: Ofer Yodfat, Modi'in (IL); Illai J Gescheit, Tel Aviv (IL); Iddo M. Gescheit, Tel Aviv (IL)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 144 days.

(21) Appl. No.: 14/619,207

(22) Filed: Feb. 11, 2015

(65) Prior Publication Data

US 2015/0151041 A1 Jun. 4, 2015

Related U.S. Application Data

(63) Continuation of application No. PCT/EP2012/066368, filed on Aug. 22, 2012.

(51) Int. Cl.
*A61J 1/20* (2006.01)
*A61J 1/22* (2006.01)
*A61M 5/14* (2006.01)

(52) U.S. Cl.
CPC .............. *A61J 1/2089* (2013.01); *A61J 1/22* (2013.01); *A61M 5/1413* (2013.01);
(Continued)

(58) Field of Classification Search
CPC ............ A61M 5/1413; A61M 2205/18; A61M 2205/52; A61M 2205/502;
(Continued)

(56) References Cited

U.S. PATENT DOCUMENTS 4,259,568 A * 3/1981 Dynesen ............. G06F 15/0216
206/305
4,407,659 A * 10/1983 Adam .................... B01L 3/0227
422/926
(Continued)

FOREIGN PATENT DOCUMENTS

EP 2172182 A2 4/2010
EP 2478888 A1 7/2012
(Continued)

OTHER PUBLICATIONS

Translation of Okuda (WO 2011/033788).*
(Continued)

*Primary Examiner* — Andrew D StClair

(57) ABSTRACT

A transfer station for transferring a medical fluid between at least one supply container and at least one administration container of an infusion device is described. In an embodiment, the transfer station comprises at least one supply port configured for fluidic connection of the at least one supply container to the transfer station, and at least one exit port configured for fluidic connection of the at least one administration container to the transfer station. A transfer mechanism for automatically transferring a predetermined amount of medical fluid from the at least one supply container to the at least one administration container, and an electronic processing unit connected to an actuation means are provided with the transfer station. A processing unit controls the transfer mechanism and fluid transfer conditions according to a predetermined transfer demand entered by the actuation means.

35 Claims, 10 Drawing Sheets

(52) U.S. Cl.
CPC ....... *A61J 2205/00* (2013.01); *A61M 2205/18* (2013.01); *A61M 2205/502* (2013.01); *A61M 2205/52* (2013.01); *A61M 2209/045* (2013.01)

(58) Field of Classification Search
CPC ............ A61M 2209/045; A61J 1/20–22; A61J 1/2089; A61J 1/2096; B65B 3/003
See application file for complete search history.

(56) References Cited

U.S. PATENT DOCUMENTS

| | | | |
|---|---|---|---|
| 4,998,570 A * | 3/1991 | Strong | A61M 5/1782 128/DIG. 1 |
| 7,916,478 B2 * | 3/2011 | Tu | F16M 11/10 248/398 |
| 8,025,658 B2 | 9/2011 | Chong et al. | |
| 8,286,671 B1 * | 10/2012 | Strangis | B65B 7/28 141/9 |
| 2003/0072676 A1 * | 4/2003 | Fletcher-Haynes | A61J 1/10 422/23 |
| 2003/0078534 A1 | 4/2003 | Hochman et al. | |
| 2003/0229310 A1 * | 12/2003 | Flaherty | A61M 5/1452 604/151 |
| 2004/0112460 A1 * | 6/2004 | Stocchi | B67C 3/08 141/144 |
| 2006/0049209 A1 | 3/2006 | Baker | |
| 2006/0169348 A1 * | 8/2006 | Yigal | A61J 1/2096 141/21 |
| 2007/0198297 A1 | 8/2007 | Perkins et al. | |
| 2008/0053560 A1 * | 3/2008 | Hartman | B65B 3/003 141/2 |
| 2008/0269713 A1 | 10/2008 | Kavazov | |
| 2009/0157219 A1 * | 6/2009 | Parker, Jr | A61M 5/172 700/231 |
| 2010/0087786 A1 * | 4/2010 | Zinger | A61J 1/2096 604/224 |
| 2010/0164727 A1 | 7/2010 | Bazargan et al. | |
| 2010/0245056 A1 * | 9/2010 | Braun | A61J 1/1406 340/10.42 |
| 2011/0004143 A1 * | 1/2011 | Beiriger | A61M 1/342 604/6.11 |
| 2011/0004185 A1 | 1/2011 | Hasegawa et al. | |
| 2011/0108158 A1 * | 5/2011 | Huwiler | B65B 3/14 141/2 |
| 2012/0035535 A1 * | 2/2012 | Johnson | G01F 25/0007 604/67 |
| 2013/0035658 A1 * | 2/2013 | Haenggi | A61J 1/20 604/408 |
| 2013/0041257 A1 | 2/2013 | Nemoto | |
| 2013/0296807 A1 * | 11/2013 | Lintern | A61J 1/20 604/272 |

FOREIGN PATENT DOCUMENTS

| | | | |
|---|---|---|---|
| JP | 64-52481 | * | 2/1989 |
| JP | 2009089817 A | | 4/2009 |
| JP | 2012196342 A | | 10/2012 |
| WO | WO 2011/033788 | * | 3/2011 |
| WO | 2012019642 A1 | | 2/2012 |
| WO | 2012022771 A2 | | 2/2012 |

OTHER PUBLICATIONS

Korean Office Action dated Aug. 28, 2017, pertaining to Korean Patent Application No. 10-2015-7005325.
Japanese Office Action dated May 17, 2016, pertaining to Japanese Patent Application No. 2015-527797.

* cited by examiner

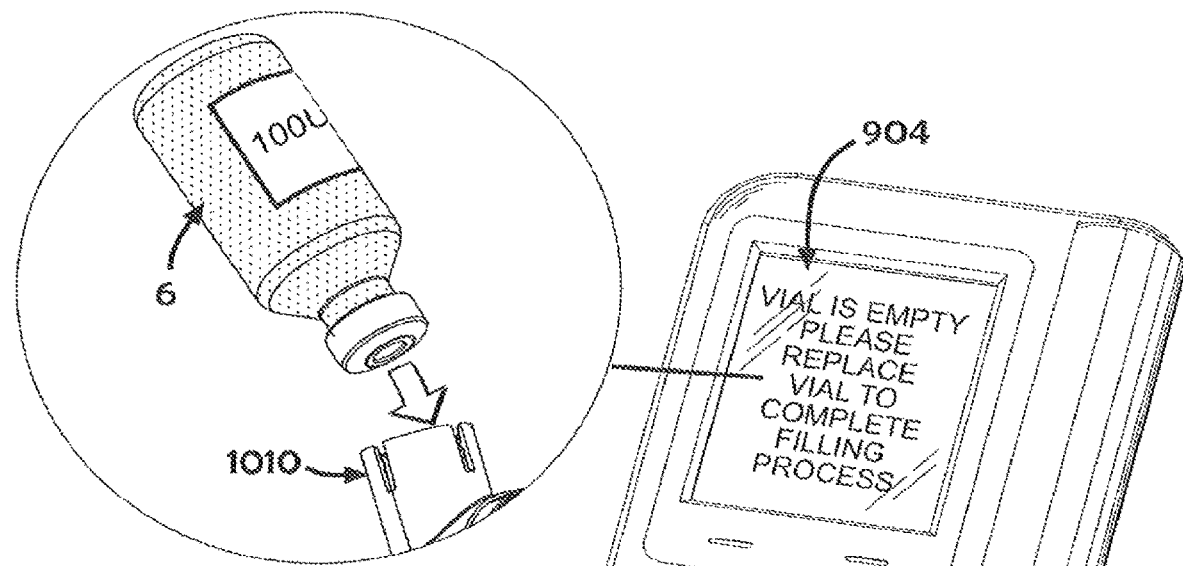
Fig. 6b
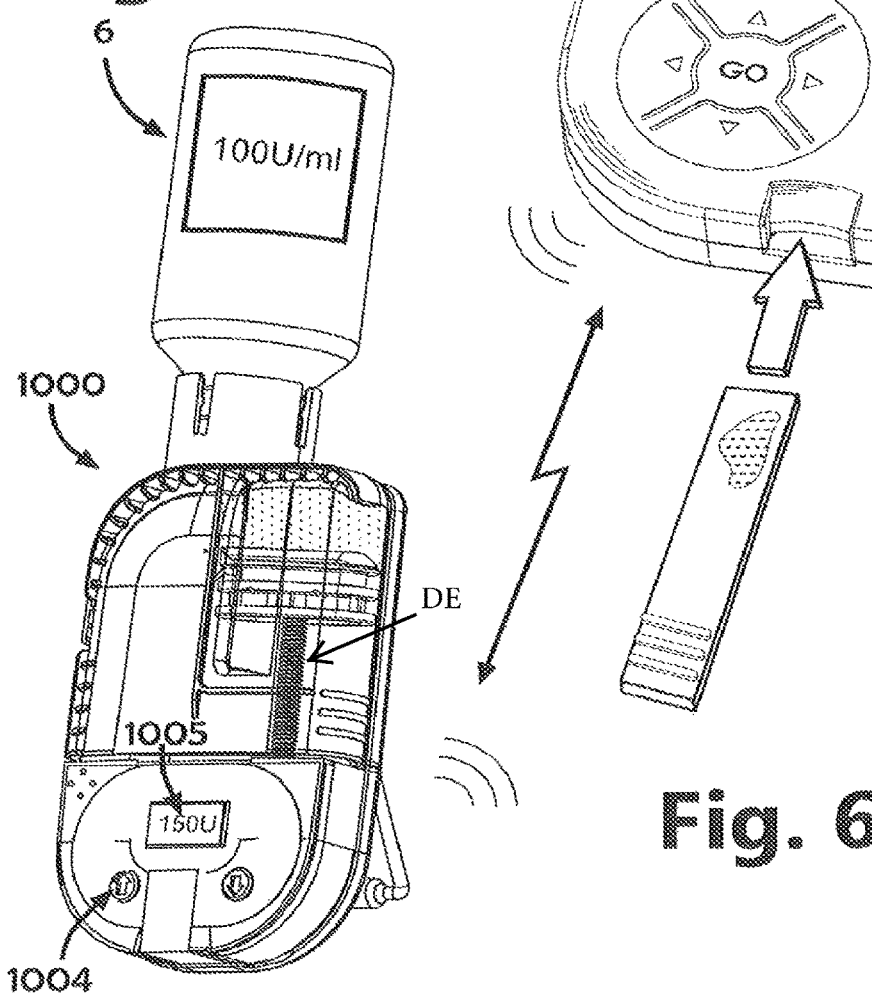
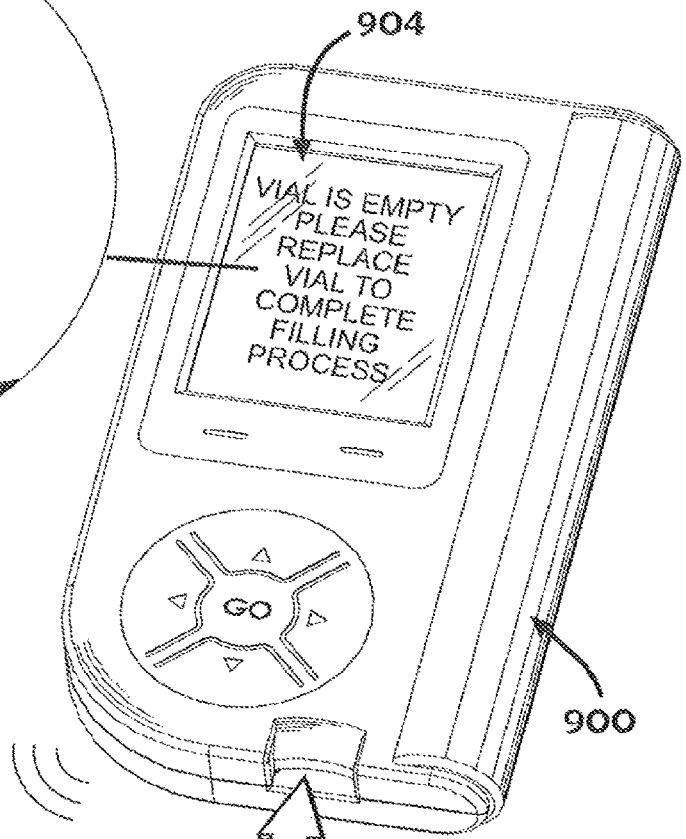
Fig. 6a

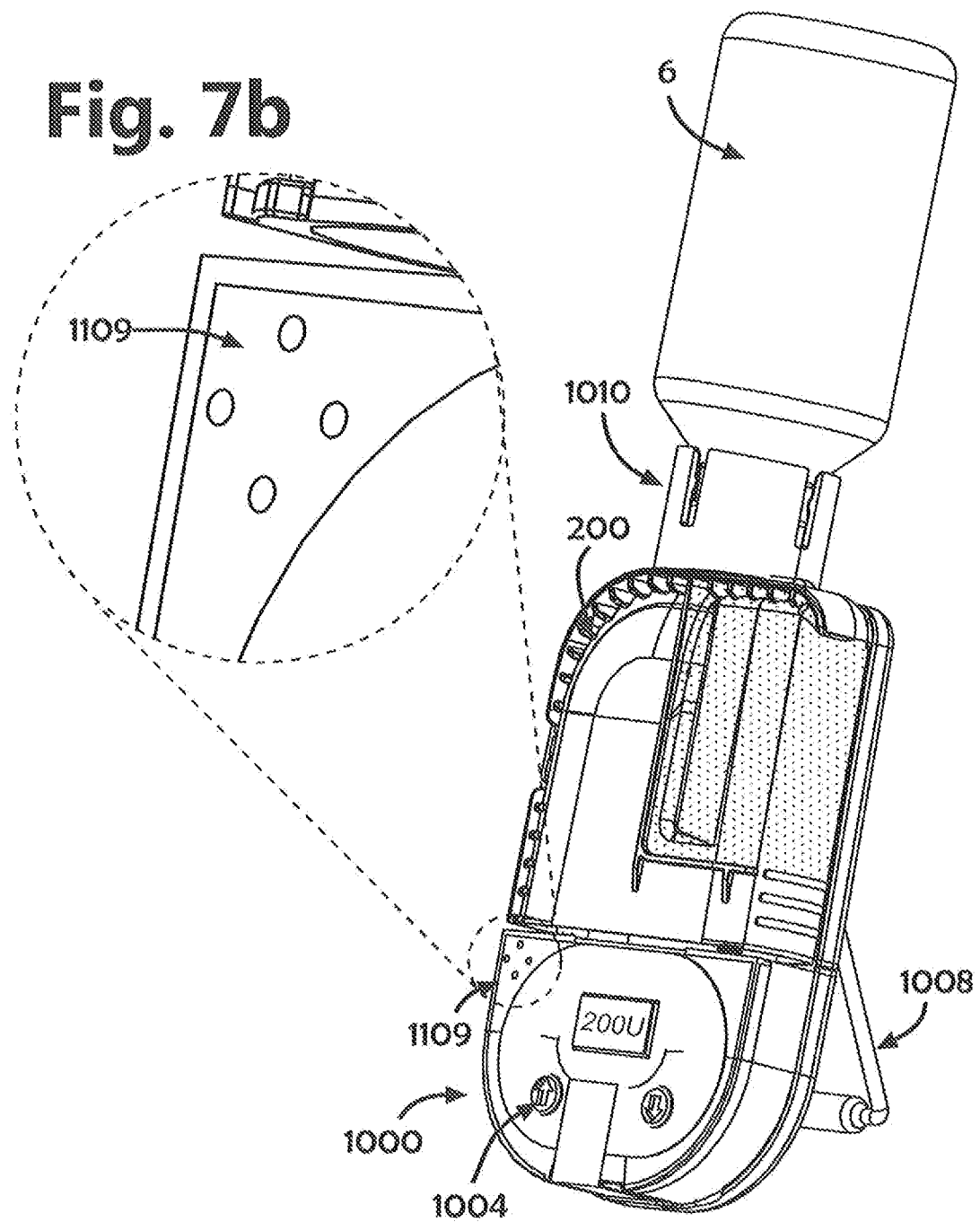

AUTOMATIC DEVICE FOR TRANSFERRING FLUID

CROSS REFERENCE TO RELATED APPLICATIONS

The present application is a continuation application of and claims priority to PCT Patent Application No. PCT/EP2012/066368, filed Aug. 22, 2012, which is hereby incorporated by reference in its entirety.

TECHNICAL FIELD

The present invention relates to a transfer station for transferring fluid between a supply container and an administration container of a medical device, in particular for transferring insulin from a supply container to an administration container of an infusion device such as a pump, and a method of transferring fluid between a supply container and an administration container.

BACKGROUND

Most administration devices like insulin pumps and reservoirs thereof are filled manually. Some devices require the user to withdraw a medical fluid like insulin from a vial into a syringe first, and then inject the medical fluid into the reservoir. An example of such a device is e.g. shown in US 2011/0004185 A1. Other more advanced devices allow the direct connection of an insulin vial to an adapter and then to the administration device. The filling can be done by pulling a rod with a handle or withdrawing the insulin from the vial into the reservoir via the adapter. After filling, the user should check if the amount of medical fluid is correct and verify that no air bubbles entered the reservoir. The existence of air bubbles might cause occlusion of the administration device and delivery inaccuracy problems. Current configurations of filling adapters and options, require long-term training of the user, and they experience many problems and misfiling until they are skilled to do the filling properly. They are led by trial and error and waste insulin, time and expensive disposable part in the process. They also cause unintentional pricking.

SUMMARY

According to at least one embodiment of the present disclosure, a transfer station, a transfer system, and a method for transferring a medical fluid between at least one supply container and at least one administration container are disclosed.

In at least one embodiment of the present disclosure, a transfer station for transferring a medical fluid between at least one supply container and at least one administration container of an infusion device is disclosed. The transfer station comprises at least one supply port configured for fluidic connection of the at least one supply container to the transfer station, at least one exit port configured for fluidic connection of the at least one administration container to the transfer station, and a transfer mechanism for automatically transferring a predetermined amount of medical fluid from the at least one supply container to the at least one administration container, and an electronic processing unit connected to an actuation means are provided. In at least one embodiment, the processing unit controls the transfer mechanism and fluid transfer conditions according to a predetermined transfer demand entered by the actuation means.

In at least one embodiment of the present disclosure, a transfer system is disclosed. The transfer system comprising at least one supply container, at least one administration container, and an embodiment of a transfer station of the present disclosure.

In at least one embodiment of the present disclosure, a method for transferring a medical fluid between at least one supply container and at least one administration container is disclosed. In at least one embodiment, the method comprises fluidly connecting the at least one supply container and the at least one administration container to a transfer station, the transfer station comprising a transfer mechanism and an electronic processing unit connected to an actuation means. Additionally, the method comprises setting a transfer demand with the actuation means, and automatically transferring the medical fluid from the at least one supply container to the at least one administration container, wherein the processing unit controls the transfer mechanism according to the transfer demand entered by the actuation means. Optionally, the method may repeat one or more times the steps of transferring a small amount of fluid and transferring back the small amount of fluid. Lastly, the method comprises transferring the demanded amount of medical fluid to the at least one administration container.

BRIEF DESCRIPTION OF THE DRAWINGS

FIGS. 6a and 6b show schematic illustrations of an indication process according to at least one method for transferring a medical fluid of to the present disclosure.

FIGS. 7 and 7b show three-dimensional views of an embodiment of a transfer system for transferring a medical fluid according to the present disclosure.

FIG. 8b shows a detailed three-dimensional view of the adapter for two supply containers according to FIG. 8a.

Figure 1:
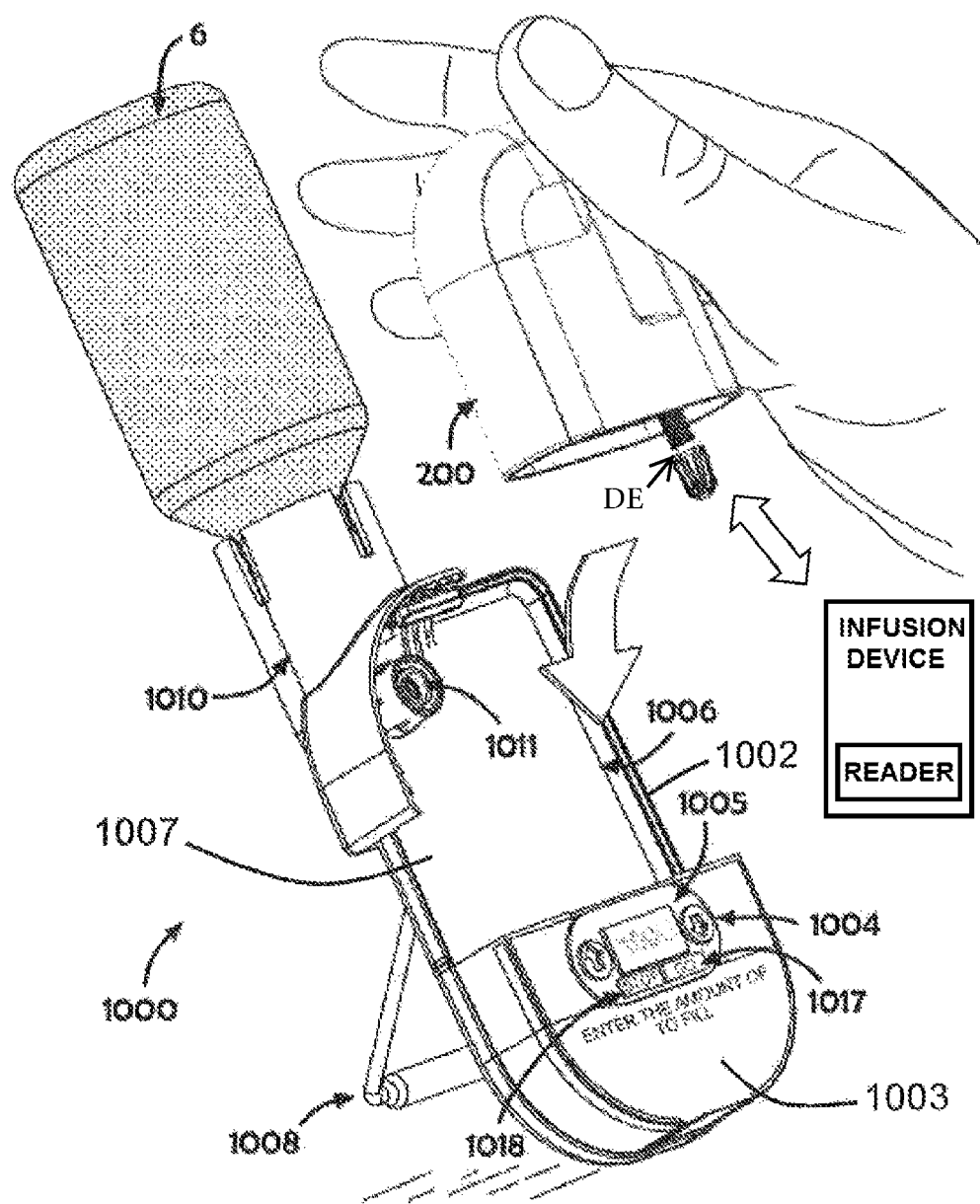
FIG. 1 shows a three-dimensional view of a transfer system for transferring a medical fluid according to at least one embodiment of the present disclosure.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

According to at least one embodiment of the present disclosure, a transfer station and a system for transferring a medical fluid between a supply container and an administration container of an infusion device are disclosed. In at least one embodiment, the transfer station or system provides a required amount of medical fluid in the administration container, avoids air within the administration container and provides convenient and accurate filling of the administration container of the infusion device. Further, in at least one embodiment a method for transferring a medical fluid between a supply container and an administration container of an infusion device is disclosed In at least one embodiment of the transfer station, the transfer station comprises at least one supply port for fluidic connection of at least one supply container and at least one exit port for fluidic connection of one or more administration containers with the transfer station. One or more supply containers may be directly connected to the at least one supply port or an adapter or conduit may be used between the supply containers and the supply ports. The at least one port for the supply container and the port for the administration container are fluidly connected within the transfer station by a conduit. The conduit may comprise further devices like a valve, a mixing device, a filter or the like. The transfer station comprises a transfer mechanism for automatically transferring a predetermined amount of medical fluid from the at least one supply container to the administration container, and an electronic processing unit comprising an actuation means or being connected to an actuation means respectively. The processing unit controls the transfer mechanism according to a predetermined transfer demand. The user, or the pump in a closed-loop configuration, may send commands to the processing unit which in turn performs the transfer.

After entering the predetermined transfer demand via the actuation means (e.g. one or more buttons, a capacitive or resistive touch screen surface, voice commands or voice recognition) by the user or for example by a medical monitoring device or the like, the transfer of the fluid is accomplished by the transfer station without any further participation of the user. In an embodiment, the user only has to initiate the fluid transfer by entering the transfer demand (for example by pressing a go-button). In another embodiment a user can further enter or input transfer demands such as setting, confirming or changing a desired amount of medical fluid. For example, the user can define a specific time for filling, or choose from a set of therapeutic fluids which one to fill in the reservoir/container or which ones to mix, or in which proportions, etc. Also the medical monitoring device may set the transfer demand automatically without any action of the user. Furthermore a fixed amount of fluid may be preset in the transfer station and may be filled automatically as soon the administration container and the supply container are connected. It is observed that the automatic filling device can have an option to identify if the reservoir being connected has already some amount of insulin in it, to inform the user, and to calculate the difference (delta) of fluid to be transferred in order to reach the requested amount of fluid set by the user.

With the manual filling or reservoirs for providing insulin to a patient by an administration device like a pump there is the risk of inaccurate filling of insulin units to the reservoir. No accurate indication of the amount filled to the reservoir is available prior to connection of the reservoir to the pump. Having an automatic filler communicating with the pump, there is created a double check about the amount in the reservoir. The pump identifies how much insulin is in the reservoir and verifies with the filler. This configuration constitutes a safety feature.

Alternatively the transfer station may comprise a readout means to read a transfer demand, or other information about the amount of fluid to be transferred, from an information means such as an RFID provided on the administration container.

The transfer station may be used in a transfer system for transferring medical fluid from at least one supply container to one or more administration containers used for an infusion device. In at least one embodiment, the system comprises at least one supply container, one or more administration containers and the transfer station. Optionally, the system may further comprise the infusion device, a remote control device, an external medical monitoring device, a blood sugar measuring device or other devices advantageously used in the treatment of diabetes and administering insulin to a patient.

A tag or marking may be provided by a token, RFID-signal or key. The tag can be modifiable or not (i.e. data can be read and/or written). Accordingly, the infusion device may comprise a readout means for reading the tag or marking.

In at least one embodiment of the present disclosure, the administration container is provided with a (modifiable) tag or a marking, indicating that the administration container has been filled automatically according to a predetermined transfer demand. The tag or the marking can also indicate that the administration device has not been filled manually or to the opposite that it has not been filed automatically. The data associated with the tag can indicate in which conditions filling operations have been conducted (partly manually and or partly automatically according to the present disclosure).

According to at least one embodiment, the rod movement can be allowed only if (and after) the tag recognition has been performed. The tag or marking also can be handled by the transfer station e.g. after completion of the fluid transfer.

In case where a non-automatically filled administration container is identified by the readout means, i.e. there is no automatic filling tag, the administration mechanism of the infusion device may be blocked, a warning signal may be given to indicate the manually filled administration container or only a degraded mode of operation of the infusion device is activated. Thus, the transfer station may provide for authorization for the infusion device to start or to operate the administration of fluid to a patient. The infusion device may send an alert to the monitoring device.

In at least one embodiment, the infusion device can work in a conditional operation mode: only in the case of the administration container has been filled automatically, the associated infusion device is ready to provide full or normal service. In the other case the infusion device can operate in a reduced service mode or not at all. The device may not work and it may not be allowed to work.

A conditional downstream operation of the infusion device, depending on the filling conditions, enables control over the safety of the global system.

For example, if not properly filled, the infusion device may not be able to reliably deliver the basal (small volumes), but it may be able to deliver boluses (that represent higher volumes and may be less impacted by the presence of some air bubbles). Such a configuration may lead to a warning or notification (display, sound or the like). Another possible service mode can mean that certain actions can be limited or forbidden (for example, the display capacities can be modified, or certain options in the menu cannot be displayed, or the occlusion detection system—if any—can be activated, etc.). In particular, the fluid transfer being controlled, there exists the ability to authorize (allow, permit, enable) the operation of the infusion device. It also exist the possibility to limit or modify the functioning of the infusion device.

In at least one embodiment, delivery can be authorized or allowed in certain cases only, for example when certain predefined filling criteria are met. Predefined filling criteria can be based on data associated with one or more filling operations, wherein the data is selected from the group consisting of: duration of filling operations, average speed of filling operations, profile of filling including a plurality of filling sequences and associated filling speeds operations, inclination during filling operations, movements during filling operations as assessed by one or more accelerometer devices, temperature during filing operations, status data on complimentary or partial or complete filling operations and any combination thereof.

For example the pump may not be authorized or allowed to operate (or function or work) if the filling has been assessed as having been performed by unauthorized devices or certain devices (not automatic ones, not compatible ones, less accurate ones, etc.). In other embodiments, certain functions of the pump may be allowed while other may be forbidden (or even not displayed as accessible functions on the user interface). For example, if not automatically filled, only bolus buttons can be activated. In an embodiment, an alert is emitted if the one or more filling criteria are not met.

In at least one embodiment, the use of the infusion device is disallowed if one or more predefined filling criteria are not met. In another embodiment, the functioning of the infusion device is modified if one or more predefined filling criteria are not met. In a development, the infusion device is provided with a display and wherein the display providing access to functions of the infusion device is modified if one or more predefined filling criteria are not met. In an embodiment, the functioning of the infusion device is allowed or permitted or enabled or authorized if one or more predefined filling criteria are met. In another embodiment, one or more operations performable by the infusion device are allowed to be performed if one or more predefined filling criteria are met. An operation of the infusion device can be a basal injection operation or a bolus injection operation.

In at least one embodiment, the transfer station is password or passcode protected. The system may ask the user to enter an activation code (either to bypass or to confirm such controls about filling conditions). For example, this feature can be used to control the filling operation made by children or teenagers. This parental control or safety enables to avoid possible false or wrong or improper filling to take place (only one of the parents or the physician can be allowed to use the automatic device). An activation code also can enable the bypass of unmet filling conditions. The activation thus can be a password for gaining access to a functionality; it also can serve to gain super administrator rights.

In an embodiment, the user can scan the bar code on the alternative (or second) filling device (which does not present the features presently described). Having access to or having stored the information of an inappropriate filling operation, the infusion pump or delivery device can downstream handle other functions or behaviors. The pump or delivery device can manage the different probability of the occurrence of an occlusion. For example, the pump can emit a notification error and further correct one or several injections due to the possible presence of air bubbles in the system.

In at least one embodiment, the user can choose between automatic filling and manual filling, by using the remote control.

In at least one embodiment, since the presence of air bubbles is mastered (at least for initial filling and assuming degassing due to temperature is also handled or managed or controlled by the delivery device), the delivery device may omit a costly and complex occlusion detection system in the pump (thereby reducing the complexity and cost of manufacturing of the delivery device).

The actuation or input means for entering a transfer demand, e.g. for starting the automatic transfer of the medical fluid or for setting a required dosage of the medical fluid, can be provided by at least one control button or navigation button, which can be actuated manually. Also the actuation means can be provided by an actuation signal sent to the processing unit from outside the transfer station. The actuation signal may be sent from a remote control device or via an electrical connection from a medical monitoring device or the like. Furthermore the actuation signal can be entered by voice demands, such that the transfer station can be activated by talking.

In at least one embodiment of the method of the present disclosure, the method for transferring a medical fluid between a supply container and an administration container of an infusion device comprises only very few steps and interaction of a user. First, at least one supply container and an administration container are fluidly connected to the transfer station, which comprises the transfer mechanism and the electronic processing unit connected to an actuation means. Then a transfer demand is set to the processing unit by the actuation means. An amount of medical fluid to be transferred to the administration container is determined, like e.g. 100 units of insulin, and stored in the e.g. in the processing unit, or a required amount of fluid can be determined by the actuation means. Finally, the demanded amount of medical fluid is automatically transferred from the at least one supply container to the administration container, wherein the processing unit controls the transfer mechanism according to the transfer demand entered by the actuation means.

The transfer of the medical fluid according to the disclosed method when using a transfer station as disclosed above requires less steps in the filling process (compared to manual and traditional ones). The user is able to set an exact amount he would like to fill and exactly this amount is transferred automatically without further supervision. Instructions necessary to handle the transfer station are reduced to a minimum. Furthermore the method and the system disclosed are environmental friendly, since the number of disposable parts and plastic waste is reduced.

In at least one embodiment, the transfer station comprises a housing with a first housing chamber accommodating at least the transfer mechanism and the processing unit and a second housing chamber for at least partially accommodating the administration container. First and second housing chambers are an integral part of the housing. At least one control button is accessible from outside the first chamber for the entry of at least one transfer demand. The first chamber may be designed as a closed box. The second chamber may be open on one side for introducing the administration container into the free volume of the second chamber. The second chamber can comprise a support plate, which serves as a supporting surface for the administration container, and a side wall at least partially surrounding the plate, which at least partially encompasses the administration container. It also can be a closed chamber with a door, to insert the administration container.

The second chamber may comprise a releasable fastening means for securely fastening the administration container in the chamber. The fastening means may e.g. be designed as a snap fit between the chamber and the container. A retaining means for retaining the supply container or an adapter for a plurality of supply containers may be arranged at the second chamber of the housing. The retaining means may be designed as a tube like extension projecting from the second chamber in a longitudinal direction of the housing. The supply port for the supply container and the exit port for the administration container are located in the second chamber of the housing, preferably close to an edge of the housing. The conduit for connecting supply port and exit port is arranged at the housing as well. When the supply container is fixed on the supply port, e.g. simply by introducing the supply container into the retaining means, and the administration container is introduced into the second chamber and fixed with its inlet on the exit port of the housing, the supply container and the administration container are automatically fluidly connected with each other. The ports can be realized in a conventional manner, e.g. by piercing a septum, opening a valve or the like.

Further the transfer station can comprise an up-button and a down-button for setting a transfer demand such that the up-button and the down-button increase and decrease a demanded amount of medical fluid to be transferred respectively. Pressing the up-button e.g. increases the number units of an amount of insulin to the transferred, whereas the down-button decreases the number of units. Also the transfer station may comprise a go-button and a stop-button for manually initiating and terminating a transfer process respectively. Alternatively an embedded keyboard can be provided to directly enter a numeric value of the amount to be retrieved. The keyboard can also be also an external keyboard connected via USB, wirelessly or the like. Alternatively the same button may be used to initiate and to stop the process alternating. Further a display can be connected to the processing unit for displaying a set transfer demand and/or a transfer status of the transfer station. For example the display indicates the number of units of the medical fluid, which will be transferred, or the display indicates that the transfer is complete or could not be completed, for example because the supply container was empty before a complete transfer. All navigation buttons, like the up-button, the down-button, the stop-button and the go-button, and also the display advantageously are provided on the first chamber of the housing close the processing unit. The navigation buttons and the display are convenient to set a required amount of fluid and to control the transfer of the fluid during the transfer or afterwards. This input method also can be fulfilled by the use of a touch screen.

Furthermore the transfer station may be provided with a tactile and/or audible indicator for indicating a transfer status of the transfer station by a tactile or an audible signal. A vibrator may serve as a tactile indicator and a sound like a beep may serve as an audible indicator. These signals allow sightless or deaf persons to fill the administration container easily by sound or tactile recognition and control. The disclosed automatic filler helps visually impaired persons (persons with diabetes may have vision problems).

In at least one embodiment of the transfer station, a motor is provided for driving the transfer mechanism according to a command of the processing unit. The motor may be an electromotor such as a linear motor or the like. The transfer mechanism basically may comprise a push or pull rod driven by the motor. The transfer mechanism acts on the administration container to create a filling force like a negative pressure to suck in the medical fluid from the supply container via the supply port, the conduit and the exit port leading to the administration container. Also the transfer mechanism may act on a driven element supported in the administration container, e.g. a piston rod, such that a transfer force is exerted via the driven element. Thus the transfer mechanism interacts with the driven element of the administration container and exerted transfer force transfers the fluid to the administration container. Thus elements of the administration container normally used for administering the medical fluid from the container to a patient by an infusion device can be used for automatically transferring the medical fluid from the supply container into the administration container.

The transfer station may additionally comprise an antenna for receiving and/or transmitting signals, e.g. for remote control of the transfer station such as entering a transfer demand. Also, the antenna can serve for wireless communication with a medical device or electronic monitoring device. For example, a demand signal may be sent wirelessly from the transfer station to the infusion device or as an instant message, e-mail or short message to a cellular phone, pocket computer or the like. Also, the medical device or electronic monitoring device may serve as the actuation/input means for entering the predetermined transfer demand. Signals may be transmitted to a medical observation device, which for example runs a fluid management program or stores history data for future fluid administration calculations. Thus the transfer station or the system including the transfer station can be part of a health management program and reduces the number of input actions for the user. For example a user may set filling programs in advance according to different activities or times of the day and the corresponding transfer demand is automatically entered into the transfer station. Also data may not be lost and the fluid administration can be managed reliably without the need of regular input of the user.

In at least one embodiment of the present disclosure, the transfer station further comprises a support that extends in an angled position from the housing such that the transfer station is supported in a partially vertical position, that means in an at least partially upright position with the supply container arranged above the administration container. In the angled position the support defines an angle α to the housing of $0 \leq \alpha \leq 90°$. In the at least partially upright position the supply container is situated above the administration container in a vertical direction and the exit of the supply container is orientated downwards in direction of the administration container. Thus air existing inside the supply container is located at the opposite side of the container exit and cannot pass through the exit and the supply port into the transfer station and the administration container.

The support may be designed as a bow or bracket, which is attached on one end to the housing. The support also may comprise several bows, brackets or legs, which together support the transfer station in the upright position. The opposite end serves as a first base, which rests against the ground. One edge of the housing may serve as a second base, which also rests against the ground. Thus the transfer station is supported by the projecting support end and the edge of the housing such that it stands up in a nearly or fully upright position. The support can be arranged pivotally at the housing. For example the end of the support attached to the housing is provided with a hinge. Thus the support can be fold up and requires less space. The hinge may provide several predetermined positions for the support, such that the support extends from the housing in different predetermined angled positions. In this way the transfer station can stand up in different more or less upright positions. For example a spring mechanism may fix the support in a specific angled position.

A transfer of medical fluid while the transfer station is in an at least partly upright position can reduce air bubbles and cavitation within the reservoir. Thus the accuracy of the transferred amount of fluid is improved.

As mentioned before, an adapter may connect more than one supply container to the transfer station. The adapter may comprise several entry ports for the attachment of several supply containers. The entry ports are connected to fluid lines inside the adapter. The fluid lines may end in one common outlet port, which can be connected to the supply port of the transfer station. The adapter may be a disposable part.

Also the supply port may be designed as a separate part, which is connectable to the housing. Therefore the supply port may be replaceable. For example different kind of supply ports may be provided, which suit for different kind of adapters or housing design. The supply port also may comprise more than one port connection to connect more than one administration container to the transfer station. That means filling of more than one administration container at same time or one after the other is possible. For example, a concomitantly filling from different supply container is also possible.

When using the method for transferring a medical fluid between a supply container and an administration container according to the present disclosure an amount of medical fluid can be transferred by the transfer mechanism according to a predetermined transfer velocity controlled by the processing unit. Thus for example a constant velocity can be provided for the fluid transfer, which avoids the generation of air bubbles in the administration container. In another embodiment, a sensor can check the status of air bubbles and alter or modify the filling velocity accordingly. In another embodiment with memory and computing means, a learning system can be implemented. Alternatively the processing unit may provide for a velocity profile (i.e. by linear segments or by functions or curves) for filling the administration container. For example the transfer may be faster in the beginning than in the end of transfer process.

In at least one embodiment, an indication is provided when the supply container will be empty before a demanded amount of medical fluid has been transferred. The indication can be provided as a text message on the display (or sent to a phone by SMS or via an email to a connected device, for example the remote control of the insulin pump or a smartphone) or as an audible or as a tactile signal. Thus the user is informed that the required amount of medical fluid has not been transferred to the administration container. A full supply container may be connected to the transfer station and the rest of the demanded amount of fluid can be transferred automatically as soon as the container is connected to the supply port or a further transfer demand is entered by the actuation means. Also the user will get a signal as soon as the full amount has been transferred. An indication can also be provided when the reservoir is full and the transfer action is completed.

Further safety features may be provided. For example, the transfer station may be provided with an attachment sensor, which verifies that the administration container is properly connected to the device. Only in case of an "ok" signal of the attachment sensor, the fluid transfer can be started. Furthermore authentication sensor for recognition of the supply container can be provided to make sure that the correct fluid is supplied. Also, an occlusion indication system may be provided.

In at least one embodiment, the medical fluid transfer method provides for an air transfer prevention process, which is automatically accomplished before the main transfer of the demanded amount of medical fluid. The air transfer prevention process is automatically initiated by the processing unit e.g. as soon as the transfer demand is entered by the actuation means. As soon as the air transfer prevention process is completed the main transfer of the demanded amount of medical fluid is started or continued automatically by the processing unit.

The air transfer prevention process may comprise the following steps. A small amount of medical fluid, which is smaller than the demanded amount of medical fluid, is transferred from a supply container to the administration container. For example a small amount of the demanded amount of medical fluid, for example a few units of fluid in case the full amount demanded is 100 or 200 units. Then the medical fluid is transferred back from the administration container to the supply container. Mostly the same small amount or an even smaller amount is transferred back. Therefore the transfer mechanism can withdraw fluid from the administration container. Optionally, the steps of transferring a small amount of fluid and transferring back of the fluid can be repeated. For example it is repeated three or four times. The volume of the small amount in each cycle may be varied by the processing unit. In any case the processing unit records the amount that has been transferred to and from the administration container so that the volume of fluid already left in the administration container can be calculated. Finally the demanded amount of medical fluid is transferred to the administration container. That means the rest of the pre-set amount of fluid is transferred in case a fraction of that amount has already been transmitted during the air transfer prevention process.

The air transfer prevention process eliminates air left in the transfer path between the supply container and the administration container. Thus the risk of air in the administration container is reduced and a precise amount of medical fluid can be transferred to the administration container of the infusion device.

After the transfer of the demanded amount of medical fluid the administration container is ejected from the transfer station, connected to the infusion device and the infusion device is preferably automatically updated with the amount of medical fluid in the administration container. Thus the infusion device is ready for administering the medical fluid to the patient.

In at least one embodiment, the infusion device can check how much insulin is left in the reservoir.

In at least one embodiment of the transfer station according to the present disclosure, all the user needs to do is place the administration container on the exit port of the transfer station. Then the user specifies the exact amount he wishes to withdraw from the supply container, which is connected to the administration container via the transfer station. To increase the number of required units, the user should push the up-button and the down-button to reduce the amount intended to be filled in the administration container. An indication of the amount filled is digitally displayed on the display. After setting the demanded amount the users presses the go-button, and filling of the administration container is processed. The transfer station is already designed to perform the filling in a position which prevents air bubbles, and includes the initial filling and dispensing to prevent air bubbles due to the air transfer prevention process. The transfer is preferably done in a constant velocity and no inertia or unwanted forces might lead to further problems in the process of fluid transfer. When the administration container is filled to the specified amount set by the user, the user will receive an audible and/or tactile indication, and an indication in his remote control. The user then can eject the reservoir, connect it to the infusion device and start the delivery of the fluid by the infusion device.

FIG. 1 shows an automatic transfer station 1000 in an upright position, ready to receive an empty administration container 200 ready for filling with a medical or therapeutic fluid respectively, e.g. insulin. After a transfer process, the administration container 200 should be connected to an infusion device (not shown) and then is connected to the user's skin via a cradle (not shown). The transfer station 1000 is connected via a supply port 1010 to a supply container 6 containing some medical fluid. The supply container 6 is connected with its fluid exit downwards, to allow easy flow from the supply container 6 to the administration container 200. The administration container 200 is connected to the transfer station 1000 via an exit port 1011 of the transfer station. The transfer station 1000 comprises a housing 1002 with a first chamber 1003 accommodating a transfer mechanism and a processing unit, and a second chamber 1007 capable of accommodating the administration container 200. The administration container 200 is supported by support plate in form of a flat surface 1006 of the housing 1002 of the transfer station 1000.

Once connected, the medical fluid is withdrawn from the supply container 6 through the supply port 1010 and the exit port 1011 of the transfer station, it is fed into an inlet port (not shown) at the bottom of the administration container 200. The user can predetermine an exact amount of medical fluid he or she would like to withdraw from the supply container 6 and transfer into the administration container 200 by pressing an up-button and down-button, designated as navigation buttons 1004 and then starts the transfer process by actuating an actuation means. In this embodiment the actuation means is given as a go-button 1017, which is pressed down to start the process. The demanded amount of fluid to be filled can be viewed on a display or screen 1005. Alternatively, the user can also choose to stop the transfer process at any time by pressing a stop-button 1018.

The upright position at which the transfer station 1000 is set is due to a support in form of an auxiliary leg 1008 located at the back of the housing 1002 and releasably fixed in a chosen angled position relative to the housing 1002. This feature will be further elaborated hereinafter.

It is important to note, that the simplicity offered by the automatic transfer station 1000 reduces the somewhat complicated steps in filling an infusion pump according to the prior art to placing the administration container 200 in the transfer station and pressing a button. It also prevents the user to be exposed to any sharp needles, which might cause unintentional pricking during the transfer process.

Figure 2:
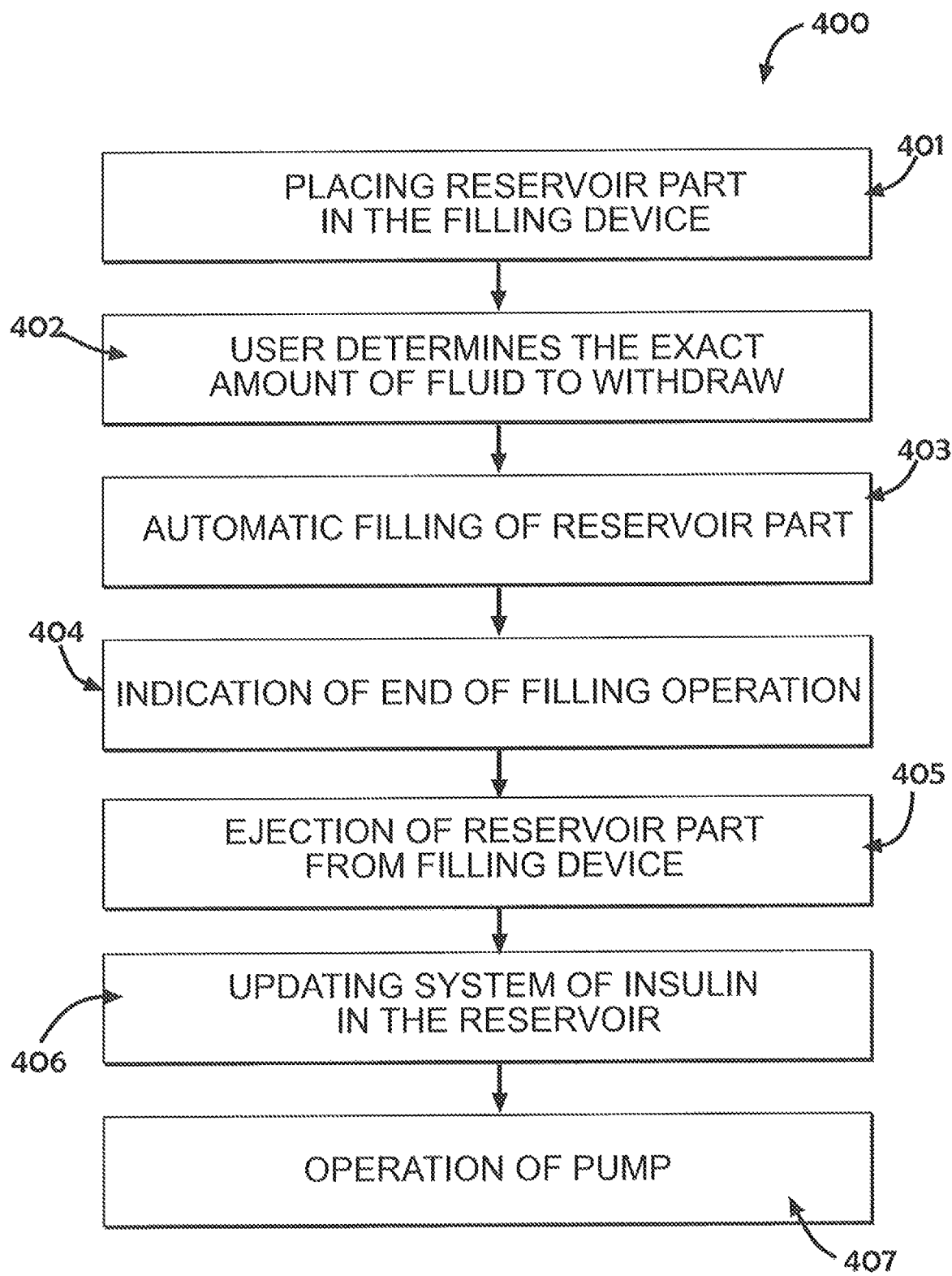
FIG. 2 shows a diagram of a method for transferring a medical fluid according to at least one embodiment of the present disclosure.

In FIG. 2 a diagram of a method for transferring a medical fluid according to a first transfer process 400 is described. In a first step 401, the user places an administration container in a transfer station making sure that a supply container is connected. Then he determines the exact amount of medical fluid to be withdrawn from the supply container in step 402, e.g. by pressing a navigation button. Thus the demanded amount of fluid is entered into a processing unit. Alternatively a pre-set amount of fluid to be transferred is already stored in the processing unit.

The determination of an accurate amount of fluid like insulin to be filled in the administration container is beneficial to all users of infusion devices. For example, users such as children need to consume smaller amounts of insulin, and therefore should have very accurate amounts in their infusion device such as an insulin pump. Moreover, filling the administration container precisely is significant also psychologically, as the user feels more secure and confident knowing that his infusion device is delivering the exact amount of fluid that he or she wanted and planned to deliver.

Then the user can initiate a transfer mechanism of the transfer station in step 403 by an actuation means. The transfer process is halted either automatically when the amount of fluid specified by the user to be filled into the administration container was filled or alternatively, when the entire volume of the administration container is filled and cannot accommodate more insulin within. The user can also stop the process at any time as described in FIG. 1 by pressing a stop-button. When transfer is done, the transfer station will provide an indication which will mark the end of transfer operation 404. The indication is either audible, tactile or the like and informs the user that the administration container is full to the amount he requested. Also the indication can be shown on a display. If the user set a false amount of insulin by mistake, he could stop the transfer process manually and determine a new amount, which the processing unit could adjust and add to or subtract from the existing fluid in the administration container. After the administration container is filled with the amount demanded, the administration container can be ejected from the transfer station in step 405. The user now can connect the administration container with an infusion device and the device is updated about the amount of insulin that the administration container contains in step 406.

The update can be done wirelessly by the transfer station sending the data directly to the infusion device or to a remote control device. After the infusion device is updated, the operation of the infusion device, e.g. a pump device, is attainable in step 407.

Figure 3:
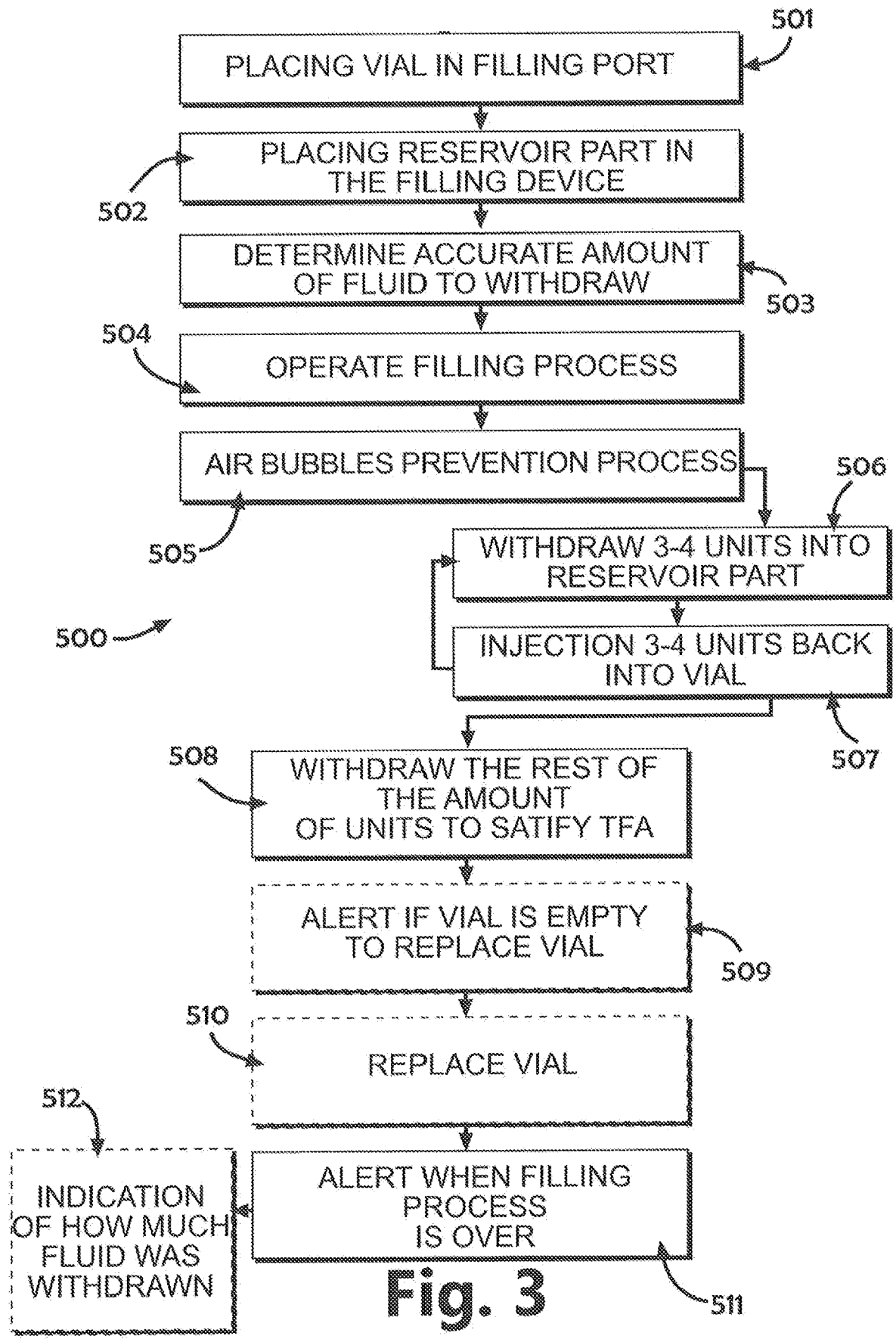
FIG. 3 shows a diagram of an alternative method for transferring a medical fluid according to at least one embodiment of the present disclosure.

In FIG. 3 an alternative automatic fluid transfer method is illustrated comprising an air transfer prevention process, which prevents air bubbles from entering an administration container during fluid transfer. Air bubbles are a phenomenon which might cause occlusion errors and additional technical errors in the drug delivery process. The method presented hereinafter offers an automatic transfer process, which allows accurate withdrawing of fluids like insulin and automatic prevention of air bubbles. This simplifies the entire troublesome process of filling the administration container, and saves insulin wasted and administration containers which might be no valid for use after the filling trial due to erroneous manual filling by the user.

In a first step 501, the user places the filled supply container in a supply port. Then, the user places the administration container in the transfer station in step 502. The user sets the demanded amount of fluid he or she would like to withdraw into the administration container in step 503. Now, in step 504, the transfer operation process is initiated by the user via an actuation means. To prevent air bubbles from entering the administration container and later on the infusion device an air bubbles prevention process 505 is applied. In step 506, the transfer station 1000 automatically withdraws a small amount of units into the administration container 200 from the supply container 6 (for example 3-4 units of medical fluid). The withdrawal is controlled by the processing unit. Then, the same amount of fluid is injected back into the supply container 6 in subsequent step 507. In some embodiments, a small amount of air is initially withdrawn prior to the transfer of fluid. Steps 506 and 507 are iterated several times as set in the processing unit, for example 3-4 iterations in order to eliminate any chance of any air bubbles, which might have been originated in the pathway between the administration container and the supply container and in particular, in the conduit which connects them. After the iterative process 506 and 507 ends, the transfer station automatically transfers the rest of the medical fluid in step 508, to comply with the demanded amount the user specified in step 503. If the supply container turns empty before the predetermined amount of fluid (Target Filling Amount) is attained, the transfer station will provide an alert to the user either audible, tactile or the like in step 509, to inform the user to replace the supply container. After the empty supply container 6 has been replaced, if needed, by a new supply container in step 510, the transfer station will continue its operation automatically to meet the predetermined amount of fluid. Alternatively, the user could choose not to continue the transfer process and cancel the rest of the action voluntarily. In either case, the transfer station will alert the user when filling is over in step 511 to inform the user he or she could eject the administration container and connect it to the infusion device. In some embodiments, this indication can wirelessly be sent to the user's remote control device or as an instant message, e-mail or SMS to its cellular phone in step 512, specifying how much insulin was transferred. The data of this specific filling process can be stored in the processing unit for future tracking.

Figure 4:
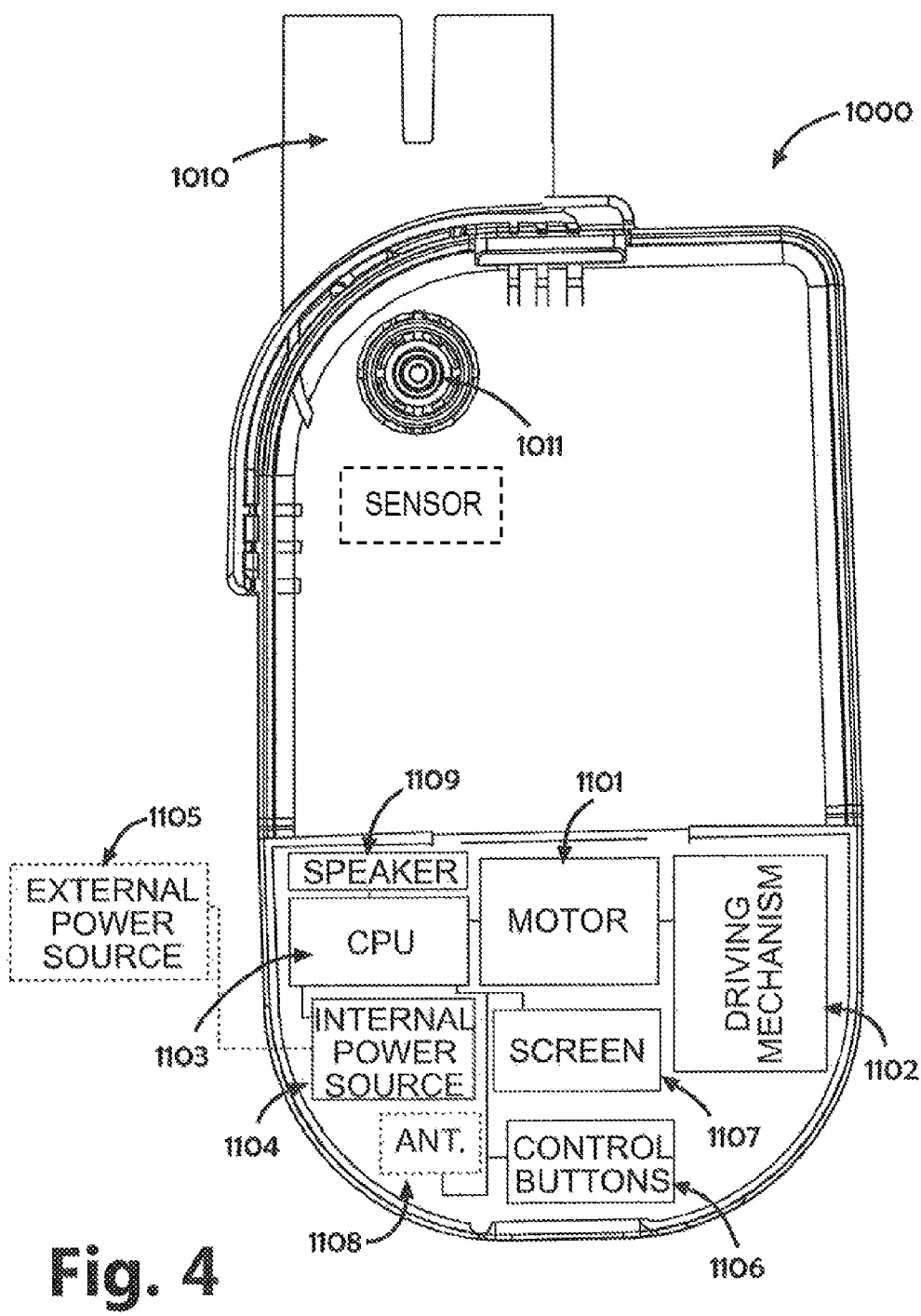
FIG. 4 shows a schematic view of at least one embodiment of a transfer station for transferring a medical fluid according to the present disclosure.

FIG. 4 is a schematic view of internal components (mechanical and electronics) of the transfer station 1000. The transfer station 1000 receives power from either an external power source 1105 (for example, the home electricity system, or any external source known in the art). Power supply could also be provided by an internal power source 1104, such as AAA batteries or any kind of rechargeable batteries or the like. The user determines the exact amount of fluid he would like to transfer by using a control buttons 1106. In addition, buttons for cancelling/stopping the transfer operation or approving the transfer operation are included as disclosed for the embodiment according to FIG. 1. Additional control buttons could also be added upon request/design in other embodiments. The user's input, data, alert alarms or any other related information can be observed on a display or screen 1107. In some embodiments, any input or output that can be achieved by using the button 1106 or/and display 1107 could be achieved by a remote control device (not shown) or any kind of smart phone or monitoring device (e.g. a laptop, iPad. etc.). This can be done with the aid of an internal antenna 1108 located in the transfer station 1000. All commands (input and output) are transferred initially to the electronic processing unit (CPU) 1103, which correlates and integrates between the different commands, operations and components of the transfer station and external units to meet the required actions. After the user has entered the input data, it is transferred from the processing unit 1103 to a motor 1101 and to activate a transfer or driving mechanism 1102, which engages with a driven element DE like a leading screw (not shown) of the administration container (not shown) resulting in the filling of the administration container. The transfer process can be done by a linear move of a piston rod or by a rotational motion of the piston rod of the motor, which will be described in details hereinafter.

Additionally, a speaker 1109 connected to the processing unit 1103 allows audible indications sent by the processing unit 1103. Alternatively this speaker 1109 could be replaced or be integrated with a vibrator or the like to provide tactile indication or any other kind of notification means.

Figure 5:
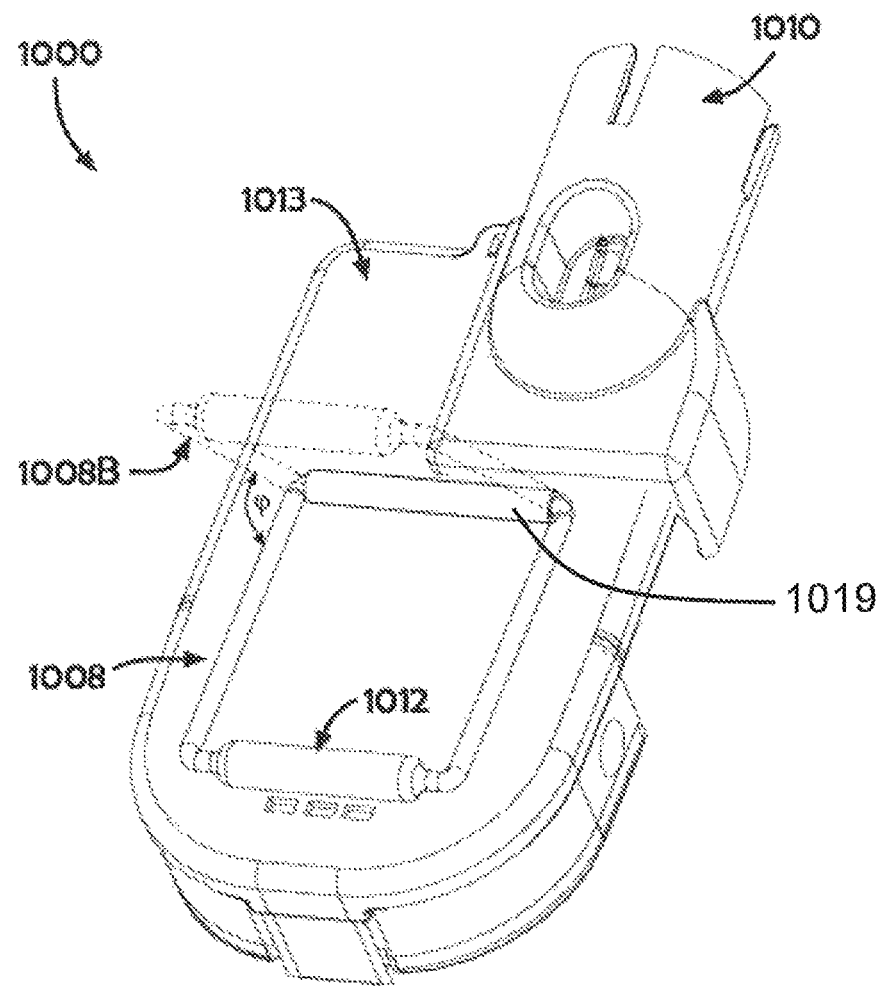
FIG. 5 shows a three-dimensional view of a back side of a transfer station according to FIG. 4.

FIG. 5 shows a back side of the transfer station 1000. On the back a flat surface 1013 of the transfer station 1000, the adjustable support in form of the supporting leg 1008 is constructed. The supporting leg 1008 is realized as a bracket, which is supported on the surface 1013 in a hinge connection 1019. The user could set the supporting Leg 1008 to an angle alpha. This stabilizes the transfer station 1000, when the administration container 200 and the supply container 6 are connected. The supporting leg 1008 is shown in an opened position in dotted lines 1008B. Most importantly the upright position, which the leg 1008 enables, allows filling of the administration container 200 with reduced amount of air bubbles. In some embodiments, a predetermined set of opening angles (for example 45 degrees and 70 degrees) will be determined according to the supply container connected (its size and the fluid it contains) and the user can choose among these set of angles. The supporting leg 1008 has a soft cushioning 1012 in the area of contact with a supporting surface such as a table. It is important to place the transfer station 1000 on a flat horizontal surface while operated. This will prevent any shocks during the transfer process which might be caused due to pressure forces (for example environmental vibrations) and the motor and transfer mechanism operations. The supporting leg 1008 will improve the accuracy of the transfer process.

FIG. 6a shows an example of wireless communication between the transfer station 1000 and a remote control device 900. The transfer station 1000 is connected to a supply container 6 of 100 units/ml. In the situation described the supply container 6 is about to turn empty. The display 1005 indicates the demanded amount of medical fluid, that the user determined to transfer into the administration container, which is 150 units in this example. Since the supply container 6 contains only 100 units/ml, it is required to replace the supply containers 6 to achieve the demanded amount of fluid. The transfer station 1000 communicates with the remote control device 900 wirelessly and through a text message that appears on the screen 904 of the remote control device 900, which informs the user that the supply container 6 is empty and requests to replace the supply container 6 with a new one, in order to complete the transfer process. As a consequence to the message the system provided, the user replaces the empty supply container 6 with a new full supply container 6 of additional 100 units/ml. The new supply container 6 is connected to the supply port of the transfer station. The transfer station 1000 continues working once the supply container 6 is replaced and after withdrawing an additional volume of 50 units, a text message will appear on the remote screen 904 indicating that the transfer process is done and that the user could eject both the administration container 200 and the half-filled supply container and he or she could store them in the right temperature and surrounding conditions to be reused to fill additional administration containers in the future.

FIGS. 7a and 7b show an alternative embodiment of a transfer station according to the present invention comprising an indication means. In this embodiment, the incorporated speaker 1109 provides an audible notification, which informs the user how much medical fluid has already been transferred to the administration container 200 and of any alarms, alerts, indications, or the like. This audible informing feature could be in aid of the visually impaired to solve problems in filling their administration container accurately and in a simple manner. The audio notifications can be further interpreted by voice systems (command, recognition, etc.) implemented in other diabetes systems, to inform a data management system.

In some embodiments, the transfer station 1000 will provide an audible indication of the updated predetermined amount of fluid to be filled and in each press up and down on the navigation buttons 1004 it will indicate the current amount of insulin that is set for filling. This will keep the visually impaired user in control and confidence that he or she does not misuse or waste any of his medical fluid. In some embodiments the indication means could be a vibrator or any other indication feature.

Figure 8A:
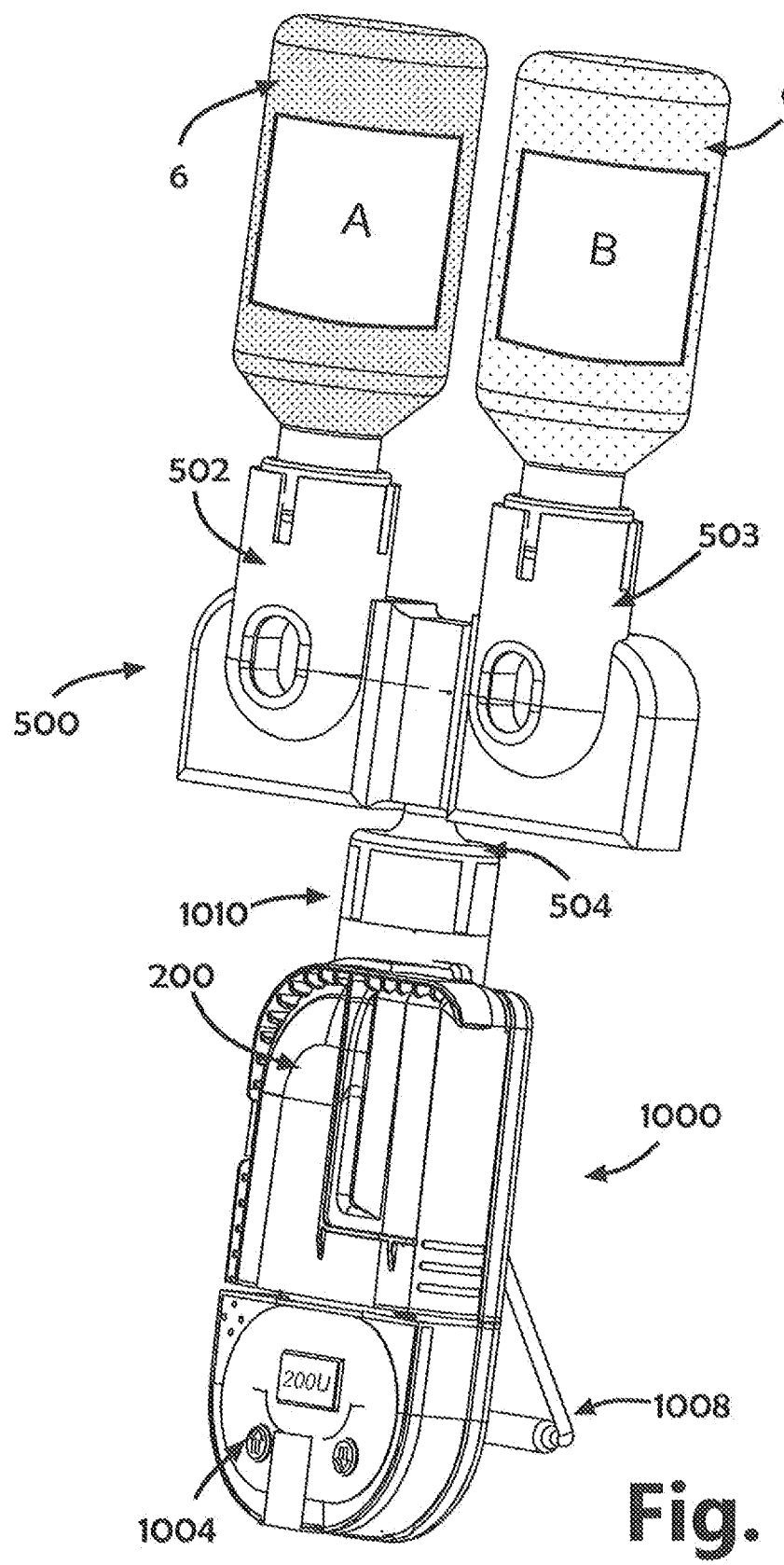
FIG. 8a shows a three-dimensional view of an embodiment of a transfer system comprising an adapter for two supply containers according to the present disclosure.

As shown in FIG. 8a, in order to avoid the replacement of supply containers 6 as illustrated in FIGS. 6a and 6b, an adapter 500 comprising at least two entry ports 502 and 503 to which a supply container 6 is connected and mounted on the supply port 1010 of the transfer station 1000. The adapter's base connector 504 fits to the supply port 1010 of the transfer station 1000. This allows the transfer of a larger amount of medical fluid. The adapter 500 also enables a mixing of two or more kinds of medical fluids directly into the administration container 200. A common example is mixing rapid-acting insulin and short or intermediate insulin in a single administration container 200. This procedure requires very careful attention when done manually and the usage of the automatic transfer station simplifies this process by allowing parallel connection of the two supply containers A and B (for example) containing different medical fluids, which are to be mixed. In certain embodiments, the mixing of one or more medical fluids will require changing the settings in the processing unit directly or by a remote control device.

In another embodiment, the adapter can fill-in a plurality of containers with the same medical fluids (or different ones).

Figure 8B:
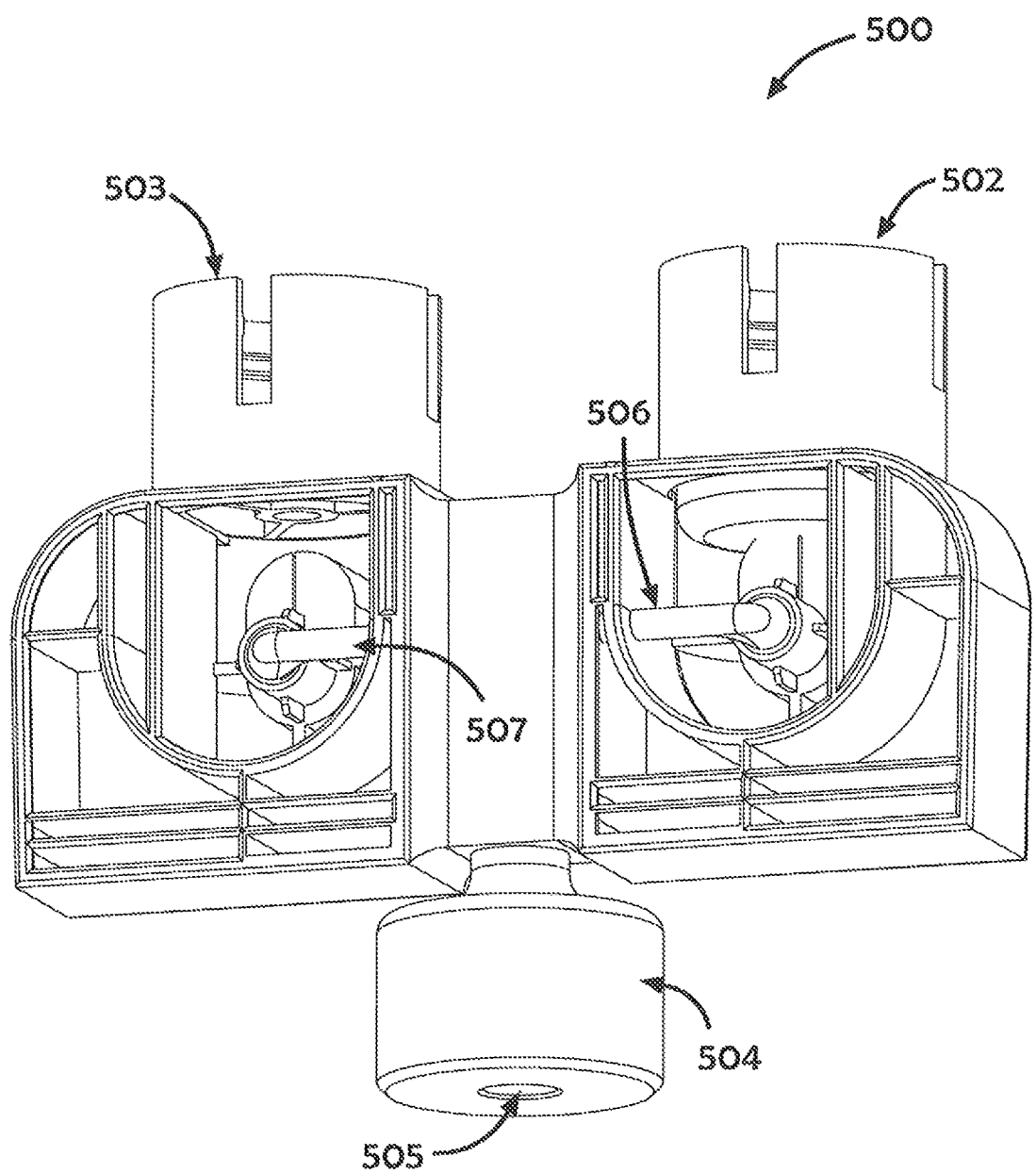

FIG. 8b shows a back view of the adapter 500 of FIG. 8a. This view shows fluid channels 506 and 507 through which the two entry ports 502 and 503 are connected to the adapter's base connector 504. The different medical fluid flows, from the two supply containers (not shown) connected to the entry ports 502 and 503 through the channels 506 and 507 and into a single channel 505 located in the adapter's base connector 504 and finally into the transfer station 1000 and ending in the administration container (not shown). In other embodiments, the adapter 500 can include more entry ports and channels, and can enable mixing of numerous fluids or transferring a larger amount of units per ml at the same time.

Figure 9:
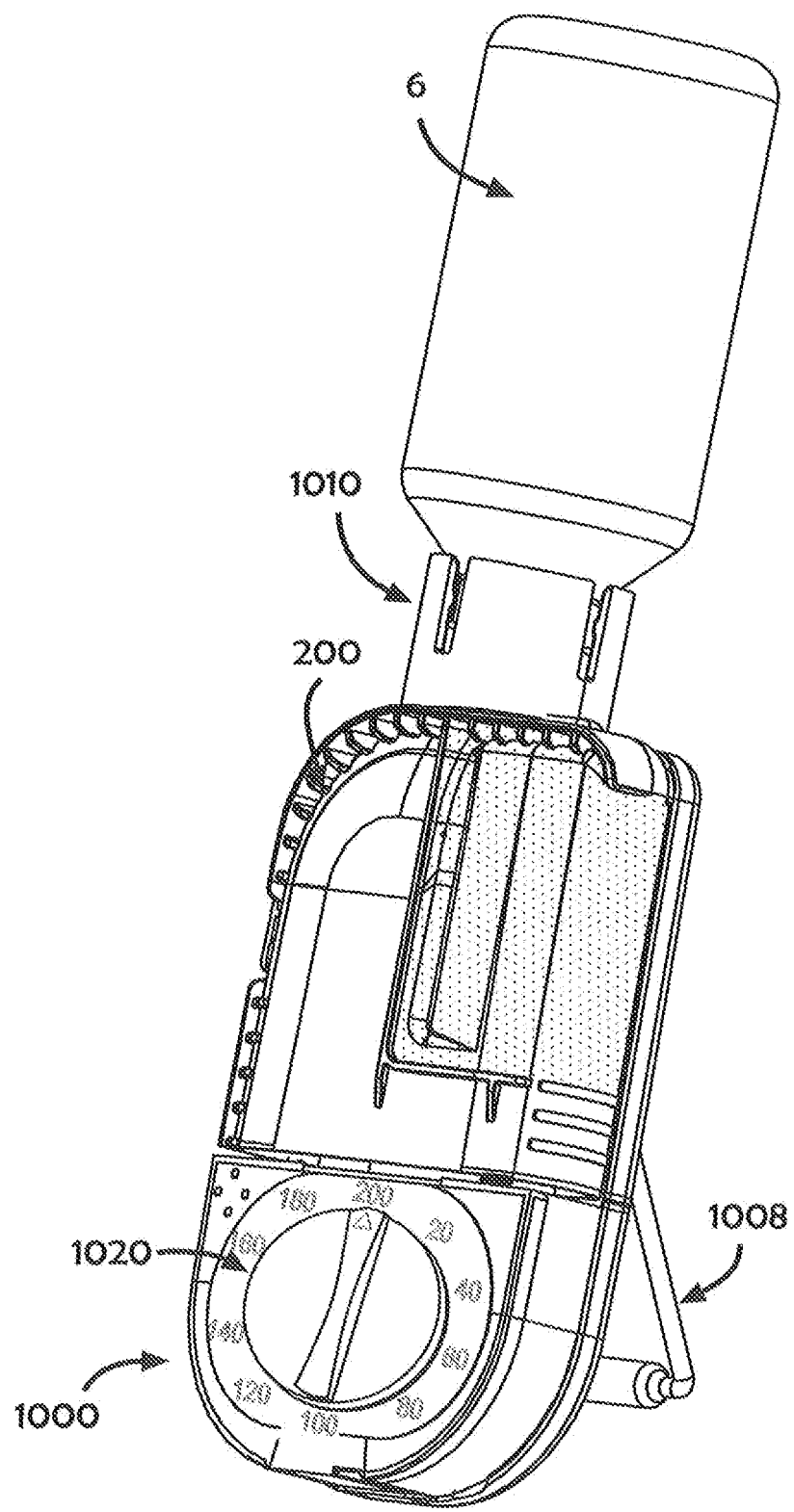
FIG. 9 shows a three-dimensional view of an embodiment of a transfer station according to the present disclosure comprising a mechanical actuation means.

In an alternative embodiment, the transfer station 1000 includes only a mechanical actuation means as shown in FIG. 9. No electronic components as specified in FIG. 4 are included. The user determines the amount of fluid he or she wishes to transfer by turning the mechanical switch 1020, which controls a spring mechanism of the transfer mechanism (not shown), which is charged to the required momentum that the user turns it. When releasing (or pressing) the switch 1020, the spring releases and the transfer mechanism is activated. The transfer mechanism moves a driven element DE of the administration container 200 resulting in filling the administration container 200 with insulin from the supply container(s) 6 mechanically. Alternatively a processing unit may be provided, which controls the release of the switch 1020 and therefore the generation of a driving force by the spring mechanism. The driving mechanism for example can be hydraulic or pressurized.

It is disclosed a transfer station for transferring a medical fluid between at least one supply container (6) and at least one administration container (200) of an infusion device comprising at least one supply port (1010) for fluidic connection of the supply container (6) to the transfer station (1000) and at least one exit port (1011) for fluidic connection of the administration container to the transfer station (1000), wherein a transfer mechanism (1102) for automatically transferring a predetermined amount of medical fluid from the at least one supply container (6) to the administration container (200), and an electronic processing unit (1103) connected to an actuation means (1106) are provided, wherein the processing unit (1103) controls the transfer mechanism (1102) according to a predetermined transfer demand entered by the actuation means (1106).

In at least one embodiment, the administration container (200) comprises a tag or marking, wherein the tag or marking is adapted to indicate that the administration container has been filled automatically according to a predetermined transfer demand by the transfer mechanism (1102).

In at least one embodiment, the housing (1002) comprises a first housing chamber (1003) accommodating at least the transfer mechanism and the processing unit, and a second housing chamber (1007) for at least partly accommodating the administration container (200).

In at least one embodiment, the actuation means (1106) is provided by at least one control button accessible from outside the first housing chamber (1003) and/or by an actuation signal sent to the processing unit from outside the housing.

In at least one embodiment, an up-button and a down-button are provided for setting a transfer demand such that the up-button increases and the down-button decreases a demanded amount of medical fluid to be transferred.

In at least one embodiment, a go-button (1017) is provided for manually actuating and a stop-button (1018) is provided for manually terminating a transfer process.

In at least one embodiment, the first housing chamber (1003) comprises a display (1107) connected to the processing unit (1103) for displaying a set transfer demand and/or a transfer status of the transfer station (1000).

In at least one embodiment, a tactile and/or audible indicator (1109) is provided for indicating a transfer status of the transfer station (1000).

In at least one embodiment, a motor (1101) is provided for driving the transfer mechanism (1102) according to a command of the processing unit (1103).

In at least one embodiment, the transfer mechanism (1102) interacts with a driven element DE of the administration container (200), which driven element DE exerts a transfer force for transferring the medical fluid.

In at least one embodiment, an antenna (1108) is provided for remote control of the transfer station (1000) and/or for wireless communication with the infusion device.

In at least one embodiment, a support (1008) extends in an angled position from the housing (1002) such that the transfer station (1000) is supported in a partially vertical position with the supply container (6) arranged above the administration container (200).

In at least one embodiment, the support (1008) is pivotably arranged at the housing (1002).

In at least one embodiment, the transfer system comprises at least one supply container (6), at least one administration container (200) for an infusion device and a transfer station (1000).

In at least one embodiment, the transfer system further comprises an infusion device, which comprises readout means for recognising a tag or marking on the administration container (200), which tag or marking indicates that the administration container has been filled automatically according to a predetermined transfer demand by the transfer mechanism (1102).

It is disclosed a method for transferring a medical fluid between a supply container (6) and an administration container (200) of an infusion device comprising the steps of: —fluidly connecting (401) at least one supply container (6) and an administration container (200) to a transfer station (1000), the transfer station comprising a transfer mechanism (1102) and an electronic processing unit (1103) connected to an actuation means (1106), —setting (402) a transfer demand by the actuation means (1106), —automatically transferring (403) the medical fluid from the at least one supply container (6) to the administration container (200), wherein the processing unit (1103) controls the transfer mechanism (1102) according to the transfer demand entered by the actuation means (1106).

In at least one embodiment, the administration container (200) is marked by a tag or marking, which indicates that the administration container has been filled automatically.

In at least one embodiment, the transfer mechanism (1102) transfers an amount of medical fluid according to a predetermined transfer velocity controlled by the processing unit (1103). In another embodiment, a sensor can check the status of air bubbles. In another embodiment with memory and computing means, a learning system can be implemented. Alternatively the processing unit may provide for a velocity profile (i.e. by linear segments or by functions or curves) for filling the administration container. For example the transfer may be faster in the beginning than in the end of transfer process.

In at least one embodiment, an indication (904) is provided when the supply container (6) is empty before a demanded amount of medical fluid has been transferred.

In at least one embodiment, an air transfer prevention process (505) is automatically accomplished before the transfer of the demanded amount of medical fluid.

In at least one embodiment, the air transfer prevention process (505) comprises the steps of: —transferring (506) a small amount of medical fluid, which is smaller than the demanded amount of medical fluid, from a supply container (6) to the administration container (200), —transferring the small amount of medical fluid back (507) from the administration container (200) to the supply container (6), —optionally, repeating one or more times the steps of transferring a small amount of fluid and transferring back the small amount of fluid, and —finally transferring the demanded amount of medical fluid to the administration container (508).

In at least one embodiment, after transfer of the demanded amount of medical fluid, the administration container (200) is ejected from the transfer station (1000), connected to the infusion device and the infusion device is automatically updated with the amount of medical fluid in the administration container (200).

The invention claimed is:

1. A transfer station for transferring a medical fluid between at least one supply container and at least one administration container of an infusion device, the transfer station comprising:
at least one supply port facing in a vertical direction and configured for fluidic connection of the at least one supply container to the transfer station;
at least one exit port facing in a horizontal direction perpendicular to the vertical direction and configured for fluidic connection of the at least one administration container to the transfer station, the at least one administration container being marked by a tag or marking, to which tag or marking data can be written and from which data can be read;
a transfer mechanism for automatically transferring a predetermined amount of medical fluid from the at least one supply container to the at least one administration container;
an electronic processing unit connected to an actuator for entering a predetermined transfer demand,
wherein the processing unit controls the transfer mechanism and fluid transfer conditions according to the predetermined transfer demand, and
wherein the transfer station writes data to the tag or marking on the at least one administration container, wherein the data comprises two or more of the following fluid transfer conditions: duration of filling operations, average speed of filling operations, profile of filling including a plurality of filling sequences and associated filling speeds operations, inclination during filling operations, movements during filling operations as assessed by one or more accelerometer devices, and status data on complimentary or partial or complete filling operations; and
a sensor which checks status of air bubbles,
wherein the processing unit provides for a velocity profile for filling the at least one administration container in which transfer of the medical fluid from the at least one supply container to the at least one administration container is faster in a beginning of the transfer than in an end of the transfer.

2. The transfer station according to claim 1, further comprising a housing having a first housing chamber accommodating at least the transfer mechanism and the processing unit, and a second housing chamber for at least partly accommodating the administration container, the second housing chamber comprising the at least one exit port, a support plate including a flat surface, and a side wall, the flat surface of the support plate configured to support a corresponding surface of the administration container, and the side wall at least partially surrounding the support plate.

3. The transfer station according to claim 2, wherein the actuator for entering a predetermined transfer demand comprises at least one control button accessible from outside the first housing chamber and/or by an actuation signal sent to the processing unit from outside the housing.

4. The transfer station according to claim 2, wherein the first housing chamber comprises a display connected to the processing unit for displaying a set transfer demand and/or a transfer status of the transfer station.

5. The transfer station according to claim 2, further comprising a support extending in an angled position from the housing such that the transfer station is supported in a partially vertical position with the supply container arranged above the at least one administration container.

6. The transfer station according to claim 5, wherein the support is pivotably arranged at the housing.

7. The transfer station according to claim 1, further comprising an up-button and a down-button configured to set a transfer demand such that the up-button increases and the down-button decreases a demanded amount of medical fluid to be transferred.

8. The transfer station according to claim 1, further comprising a go-button configured to manually actuate and a stop-button configured to manually terminate a transfer process.

9. The transfer station according to claim 1, further comprising a tactile and/or audible indicator for indicating a transfer status of the transfer station.

10. The transfer station according to claim 1, further comprising a motor for driving the transfer mechanism according to a command of the processing unit.

11. The transfer station according to claim 1, wherein the transfer mechanism interacts with a driven element of the at least one administration container, which driven element exerts a transfer force for transferring the medical fluid into a volume of the at least one administration container upon movement of the driven element internally within the at least one administration container via engagement with and actuation by the transfer mechanism.

12. The transfer station according to claim 1, further comprising an antenna configured for remote control of the transfer station and/or for wireless communication with the infusion device.

13. The transfer station of claim 1, wherein the transfer station is password or passcode enabled.

14. The transfer station according to claim 1, wherein the fluid transfer conditions under which the at least one administration container has been filled include one or more indications about one or more kinds of medical fluids with which the at least one administration container has been filled.

15. The transfer station according to claim 14, wherein the one or more indications about the one or more kinds of medical fluids relates to one or more of: a rapid-acting insulin, a short-acting insulin, and an intermediate-acting insulin.

16. The transfer station according to claim 1, wherein the transfer mechanism engages and actuates a driven element supported internally within the administration container to transfer the fluid to the administration container.

17. The transfer station according to claim 16, wherein the driven element is a piston rod.

18. The transfer system according to claim 1, wherein the velocity profile is based on functions comprising one or more linear segments or by non-linear functions comprising one or more curves.

19. A transfer system comprising:
at least one supply container;
at least one administration container marked by a tag or marking, to which tag or marking data can be written and from which data can be read; and
a transfer station comprising:
at least one supply port facing in a vertical direction and configured for fluidic connection of the supply container to the transfer station;
at least one exit port facing in a horizontal direction perpendicular to the vertical direction and configured for fluidic connection of the at least one administration container to the transfer station;
a transfer mechanism for automatically transferring a predetermined amount of medical fluid from the at least one supply container to the at least one administration container;
an electronic processing unit connected to an actuator for entering a predetermined transfer demand,
wherein the processing unit controls the transfer mechanism and fluid transfer conditions according to the predetermined transfer demand, and
wherein the transfer station writes data to the tag or marking on the at least one administration container, wherein the data comprises two or more of the following fluid transfer conditions: duration of filling operations, average speed of filling operations, profile of filling including a plurality of filling sequences and associated filling speeds operations, inclination during filling operations, movements during filling operations as assessed by one or more accelerometer devices, and status data on complimentary or partial or complete filling operations; and
a sensor which checks status of air bubbles,
wherein the processing unit provides for a velocity profile for filling the at least one administration container in which transfer of the medical fluid from the at least one supply container to the at least one administration container is faster in a beginning of the transfer than in an end of the transfer.

20. The transfer system according to claim 19, further comprising an infusion device, the infusion device comprising a reader for recognizing the tag or marking on the administration container, which tag or marking indicates that the administration container has been filled automatically according to a predetermined transfer demand by the transfer mechanism.

21. The transfer system according to claim 20, wherein the infusion device is configured to compare one or more filling conditions based on the data of the tag or marking on the at least one administration container, as read by the reader of the infusion device, to one or more predefined filling criteria, and to disallow the use of the infusion device upon one or more predefined filling criteria not being met.

22. The transfer system according to claim 21, wherein the one or more predefined filling criteria are based on data associated with one or more of the fluid transfer operations, wherein the data is selected from the group consisting of: duration of filling operations, average speed of filling operations, profile of filling including a plurality of filling sequences and associated filling speeds operations, inclination during filling operations, movements during filling operations as assessed by one or more accelerometer devices, status data on complimentary or partial or complete filling operations and any combination thereof.

23. The transfer system according to claim 20, wherein the infusion device is configured to modify the functioning of the infusion device upon one or more predefined filling criteria not being met.

24. The transfer system according to claim 20, wherein the infusion device is provided with a display being configured to modify access to functions of the infusion device if one or more predefined filling criteria are not met.

25. The transfer system according to claim 20, wherein the infusion device is configured to allow or permit or enable or authorize the functioning of the infusion device upon one or more predefined filling criteria being met.

26. The transfer system according to claim 20, wherein the infusion device is configured to allow the infusion device to perform one or more operations upon one or more predefined filling criteria being met.

27. The transfer system according to claim 26, wherein one of the one or more operations the infusion device is configured to perform is a basal injection operation or a bolus injection operation.

28. The transfer system according to claim 20, wherein the fluid transfer conditions under which the at least one administration container has been filled include one or more indications about one or more kinds of medical fluids with which the at least one administration container has been filled.

29. The transfer system according to claim 28, wherein the one or more indications about the one or more kinds of medical fluids relates to one or more of: a rapid-acting insulin, a short-acting insulin, and an intermediate-acting insulin.

30. The transfer system according to claim 19, wherein the infusion device is configured to emit an alert upon one or more predefined filling criteria not being met.

31. The transfer system according to claim 19, wherein the transfer mechanism engages and actuates a driven element supported internally within the administration container to transfer the fluid to the administration container.

32. The transfer system according to claim 31, wherein the driven element is a piston rod.

33. The transfer system according to claim 19, wherein the velocity profile is based on functions comprising one or more linear segments or by non-linear functions comprising one or more curves.

34. A transfer station for transferring a medical fluid between at least one supply container and at least one administration container of an infusion device, the transfer station comprising:
   at least one supply port facing in a vertical direction and configured for fluidic connection of the at least one supply container to the transfer station;
   at least one exit port facing in a horizontal direction perpendicular to the vertical direction and configured for fluidic connection of the at least one administration container to the transfer station, the at least one administration container being marked by a tag or marking, to which tag or marking data can be written and from which data can be read;
   a transfer mechanism for automatically transferring a predetermined amount of medical fluid from the at least one supply container to the at least one administration container;
   an electronic processing unit connected to an actuator for entering a predetermined transfer demand,
   wherein:
      the processing unit controls the transfer mechanism and fluid transfer conditions according to the predetermined transfer demand,
      the transfer station writes data to the tag or marking on the at least one administration container, wherein the data comprises two or more of the following fluid transfer conditions: duration of filling operations, average speed of filling operations, profile of filling including a plurality of filling sequences and associated filling speeds operations, inclination during filling operations, movements during filling operations as assessed by one or more accelerometer devices, and status data on complimentary or partial or complete filling operations, and
      the transfer mechanism acts on a driven element supported internally within the administration container to transfer the predetermined amount of the medical fluid from the at least one supply container to a volume of the at least one administration container upon movement of the driven element internally within the at least one administration container via engagement with and actuation by the transfer mechanism.

35. A transfer system comprising:
   at least one supply container;
   at least one administration container marked by a tag or marking, to which tag or marking data can be written and from which data can be read; and
   a transfer station comprising:
   at least one supply port facing in a vertical direction and configured for fluidic connection of the supply container to the transfer station;
   at least one exit port facing in a horizontal direction perpendicular to the vertical direction and configured for fluidic connection of the at least one administration container to the transfer station;
   a transfer mechanism for automatically transferring a predetermined amount of medical fluid from the at least one supply container to the at least one administration container; and
   an electronic processing unit connected to an actuator for entering a predetermined transfer demand,
   wherein:
      the processing unit controls the transfer mechanism and fluid transfer conditions according to the predetermined transfer demand,
      the transfer station writes data to the tag or marking on the at least one administration container, wherein the data comprises two or more of the following fluid transfer conditions: duration of filling operations, average speed of filling operations, profile of filling including a plurality of filling sequences and associated filling speeds operations, inclination during filling operations, movements during filling operations as assessed by one or more accelerometer devices, and status data on complimentary or partial or complete filling operations, and
      the transfer mechanism acts on a driven element supported internally within the administration container to transfer the predetermined amount of the medical fluid from the at least one supply container to a volume of the at least one administration container upon movement of the driven element internally within the at least one administration container via engagement and actuation by the transfer mechanism.

* * * * *